United States Patent [19]

Cesti et al.

[11] 4,278,792

[45] Jul. 14, 1981

[54] METHOD OF PRODUCING DERIVATIVES OF 6-β-AMIDINOPENICILLANIC ACID

[75] Inventors: Pietro Cesti, San Matino di Trecate; Leonardo Marsili; Carmine Pasqualucci, both of Milan, all of Italy

[73] Assignee: Archifar Laboratori Chimico Farmacologici S.p.A., Trento, Italy

[21] Appl. No.: 132,763

[22] Filed: Mar. 24, 1980

[30] Foreign Application Priority Data

Apr. 12, 1979 [IT] Italy ............................... 21809 A/79

[51] Int. Cl.³ .......................................... C07D 499/04
[52] U.S. Cl. ............................. 542/420; 260/245.2 R; 542/417; 542/419
[58] Field of Search ..................... 424/270; 260/245.2; 542/420

[56] References Cited

U.S. PATENT DOCUMENTS 3,957,764  5/1976  Lund et al. ..................... 260/245.2

OTHER PUBLICATIONS

Recent Advances in the Chemistry of β-Lactam Antibodies Special Publication No. 28, J. Elks, (Edited By) The Chemical Society Burlington House, London.

*Primary Examiner*—Nicholas S. Rizzo
*Attorney, Agent, or Firm*—Oblon, Fisher, Spivak, McClelland & Maier

[57] ABSTRACT

Method of producing derivatives of 6-β-amidinopenicillanic acid, according to which a derivative of 6-aminopenicillanic acid is condensed with a reactive derivative of disubstituted amide in an inert anhydrous solvent and in the presence of a tertiary amine. In such a reaction, the reactive derivative of the disubstituted amide comprises a complex of an amide of carboxylic acid.

4 Claims, No Drawings

METHOD OF PRODUCING DERIVATIVES OF 6-β-AMIDINOPENICILLANIC ACID

This invention relates to a method of producing derivatives of 6-β-amidinopenicillanic acid having the structural formula

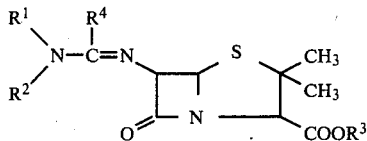

wherein $R^1$ and $R^2$ are a $C_1$-$C_4$ alkyl group, a $C_5$-$C_6$ cycloalkyl group, or $R^1$ and $R^2$ together with nitrogen atom form a cyclic group; $R^3$ is selected from a group comprising hydrogen and substituted or not substituted alkyl and aralkyl radicals; and $R^4$ is selected from the group comprising hydrogen and $C_1$-$C_4$ alkyl radicals.

Particularly, the invention relates to a method of producing compounds of formula (I), wherein $R^1$ and $R^2$ together with nitrogen atom, to which they are bonded, form a heterocyclic ring having 7 atoms, of which 6 are carbon atoms, and $R^3$ and $R^4$ both comprise hydrogen atoms, or $R^3$ is —CH$_2$OOCC(CH$_3$)$_3$ and $R^4$ is a hydrogen atom. These compounds have high antibacterial activity on the gram-negative microorganisms and are per se well known, for example being described in the British Pat. No. 1,293,590.

An exhaustive review of the several methods of preparing 6-β-amidinopenicillanic acids and esters thereof is published in the volume "Recent advances in the chemistry of β-lactam antibiotics" issued by J. Elks, The Chemical Society Burlington House, London W1VOBN.

In the above mentioned British Pat. No. 1,293,590, a method was proposed for producing derivatives of 6-β-amidinopenicillanic acid, based on the condensation of derivatives of 6-β-aminopenicillanic acid with reactive derivatives of disubstituted amides or disubstituted thioamides of carboxylic acids. Among the reactive derivatives of bisubstituted amides, the British Pat. No. 1,293,590 mentions a series of compounds that are exemplified and specifically claimed, and comprise acid amide halides, complexes of acid amides with dialkyl sulphates, or acid amide acetals.

The yields and purity of the compounds of formula I which can be obtained by using, as reactives, the acid amide halides or complexes of dialkyl sulphates and acid amides are comparatively low, as it can be readily experimentally checked.

Where the reactives used are acid amide acetals, the purity of the final compound is of reasonable degree, but the yield is still comparatively low: however, the acid amide acetals have the disadvantage of requiring a laborious two-step preparation process, as described for example in "Recent Advances in the Chemistry of β-Lactam Antibiotics", pages 25-45, 1977, issued by J. Elks, Glaxo Research Ltd., London.

Moreover, the acid amide halides and complexes of acid amides with dialkyl sulphates are highly difficult to be purified and should be stored in anydrous environment.

It is the primary object of the present invention to provide a process for preparing derivatives of 6-β-amidinopenicillanic acid of formula (I), which can be easily and readily carried out, yielding a pure final product with high yields, and uses reactives that can be easily prepared, purified and stored.

Therefore, the invention is concerned with a method of producing derivatives of 6-β-amidinopenicillanic acid having the formula

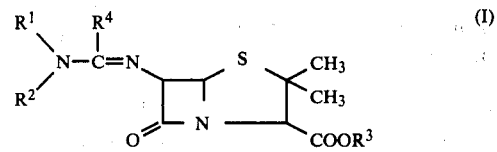

wherein $R^1$ and $R^2$ are a $C_1$-$C_4$ alkyl group, a $C_5$-$C_6$ cycloalkyl group, or $R^1$ and $R^2$ together with nitrogen atom, to which they are bonded, form a cyclic group; $R^3$ is selected from the group comprising hydrogen and substituted or not substituted alkyl and aralkyl radicals; and $R^4$ is selected from the group comprising hydrogen and $C_1$-$C_4$ alkyl radicals, according to which the condensation is carried out of a derivative of 6-aminopenicillanic acid having the formula

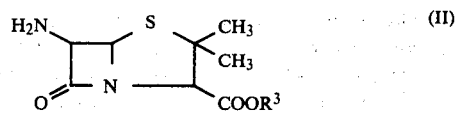

wherein $R^3$ is as above defined, with a reactive derivative of a disubstituted amide, the reaction being carried out in an inert anhydrous solvent selected from the group comprising methylene chloride and chloroform and in the presence of at least 2 equivalents of a tertiary amine, at a temperature lower than +10° C., characterized in that said reactive derivative of a disubstituted amide is a complex of a carboxylic acid amide having the formula

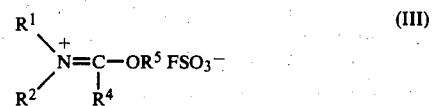

wherein $R^1$, $R^2$ and $R^4$ are as above defined, and $R^5$ is a methyl or ethyl group.

The compounds of formula (III) can be easily and long stored and are prepared in accordance with Chem. Comm. 1533, (1968)—M. G. Ahmed & R. W. Alder. These compounds are solid, generally of low melting point, and accordingly may be easily purified by crystallization. They are also provided with a very high reactivity, which enables the preparation of compounds of formula (I) by reaction with the compounds of formula (II) in very short times and with very high yields, as it will be shown by some unrestrictive examples that are hereinafter described in order to explain the method according to the invention. For the sake of greater clarity, some examples will be also given for the preparation of the reactives of formula (III) used for carrying out the method herein claimed.

EXAMPLE 1

Complex of N-formyl-hexamethylenlimine with methyl-fluoro-sulphonate 1.5 g N-formyl-hexamethylenlimine was mixed with 1 ml methyl-fluorosulphonate at 20° C. and stirred for 10 minutes. The mixture was cooled to 10° C. and a solid product was obtained, which was separated by filtering and washed with anhydrous ethyl ether. The product obtained was stable as a solid at a temperature not higher than 15° C. Yield: 2.7 g. The product obtained was of formula (III) and therein $R^1$ and $R^2$ together with N atom, to which they are bonded, form a 7 atom ring, of which 6 are C atoms, $R^4$ is hydrogen and $R^5$ is methyl.

EXAMPLE 2

6[(hexahydro-1H-azepin-1-yl)methyleneamino]penicillanic acid (MECILLINAM)

2.16 g 6-amino-penicillanic acid were added to 20 ml methylene chloride cooled to 0° C. Then 2 g triethylamine were added and stirring was continued for 2 hours at 0° C. Then, 2.5 g compound of formula (III) obtained in Example 1 were dissolved in 10 ml methylene chloride and the solution thus obtained was added to the mixture containing 6-amino-penicillanic acid. The mixture was stirred for 30 minutes at +5° C. and the disappearance of 6-amino-penicillanic acid was determined by chromatography on thin layer.

The solution was then vacuum evaporated and the residue was dissolved at 0° C. in 13 ml methyl-ethyl-ketone containing 1.9 g para-toluensulphonic acid.

The product was stirred for 2 hours at +5° C., filtered, washed with methyl-ethyl-ketone and vacuum dried at room temperature.

Yield: 3.1 g (95% theoretical).
Melting point: 156° C.
$[\alpha]_D^{20}$: +285° (C=1 in 0.1 N HCl).
I.R.: max. at 1770 cm$^{-1}$, 1680 cm$^{-1}$ and 1615 cm$^{-1}$ in accordance with the proposed structure.

By chromotography on thin layer (n-butanol-acetic acid-water 4:1:1 Merck silica gel plates) the product was identical to a sample prepared according to British Pat. No. 1,293,590 to F. J. Lund.

The compound thus obtained is of formula (I), and therein $R^1$ and $R^2$ together with N atom, to which they are bonded, form a 7 atom ring, of which 6 are C atoms, while $R^3$ and $R^4$ are hydrogen.

EXAMPLE 3

Pivaloxymethylester of 6[(hexahydro-1H-azepin-1-yl)methyleneamino]penicillanic acid (PIVMECILLINAM)

4.4 g pivaloxymethylester of 6-aminopenicillanic acid were dissolved in 30 ml methylene chloride and to the solution thus obtained, cooled to 0° C., was added 1.1 g triethylamine and 2.5 g compound of formula (III) obtained in Example 1 dissolved in 10 ml methylene chloride. The solution was continuously stirred at +5° C. for 30 minutes and then vacuum dried. The residue was crystallized from a mixture acetone-water.

Yield: 4.2 g (95.6% theoretical).
Melting point: 119° C.
$[\alpha]_D^{20}$: +231° (C=1 in ethyl alcohol).

By chromotography on thin layer (n-butanol-acetic acid-water 4:1:1-Merck silica gel plates) the product was identical to a sample prepared according to F. J. Lund's British Pat. No. 1,293,590.

The compound thus obtained is of formula (I), and therein $R^1$ and $R^2$ together with N atom, to which they are bonded, form a 7 atom ring, of which 6 are C atoms, $R^3$ is —$CH_2OCOC(CH_3)_3$, and $R^4$ is hydrogen.

This compound was converted to its hydrochloride according to known methods.

EXAMPLE 4

Complex of N,N-diethylacetamide with methyl-fluorosulphonate 1.42 g diethylacetamide were mixed with 1 ml methyl-fluorosulphonate at 20° C. The instantaneous reaction formed a white solid, which was filtered, washed with anhydrous ethyl ether and vacuum dried.

Yield: 2.7 g.
Melting point: 65° C.

The compound obtained is of formula (III) and therein $R^4$ and $R^5$ are methyl, and $R^1$ and $R^2$ are ethyl.

Instead of preparing a reactive, in which $R^4$ is methyl, by the same method a similar reactive can be prepared, in which $R^4$ is a further $C_2$–$C_4$ alkyl.

EXAMPLE 5

6[N,N-diethylacetamidine-N']penicillanic acid 2.16 g 6-aminopenicillanic acid were added to 20 ml methylene chloride cooled to 0° C. Then, 2 g triethylamine were added and stirring was continued for 2 hours at 0° C. Then, 2.35 g compound of formula (III) obtained in Example 4 were dissolved in 10 ml methylene chloride and the solution thus obtained was added to the mixture containing 6-amino-penicillanic acid. The product was stirred for 30 minutes at 0° C., then the solvent was vacuum evaporated and the residue was dissolved in a solution of 1.9 g para-toluensulphonic acid in 13 ml methyl-ethyl-ketone. The mixture was stirred for 30 minutes at 5° C., filtered, washed with methyl-ethyl-ketone and vacuum dried at room temperature.

Yield: 3 g (95.8% theoretical).
Melting point: 148°–150° C.

The compound thus obtained is of formula (I) and therein $R^1$ and $R^2$ are ethyl, $R^3$ is hydrogen and $R^4$ is methyl.

EXAMPLE 6

Complex of N-formyl-morpholine with methyl-fluorosulphonate 1.4 g N-formil-morpholine were mixed with 1 ml methyl-fluorosulphonate at 10° C. and stirred for 10 minutes.

The solid product thus formed was filtered, washed with anhydrous ethyl ether and vacuum dried at +15° C.

Yield: 2.65 g.

The product obtained is of formula (III) and therein $R^1$ and $R^2$ together with N atom, to which they are bonded, form a 6 atom ring, in which 4 are C atoms and 1 is O atom.

EXAMPLE 7

6-(morpholinemethyleneamino) penicillanic acid 2.16 g 6-amino-penicillanic acid were added to 20 ml methylene chloride cooled to +5° C. Then, 2 g triethylamine were added and the mixture was stirred for 2 hours at +5° C. Then, at 0° C. 10 ml methylene chloride were added, in which 2.6 g compound of formula (III) obtained in Example 6 were dissolved. Then, the mixture was stirred for 30 minutes at +5° C., the solvent was vacuum evaporated and the residue was dissolved in 10 ml methyl-ethyl-ketone. Then, 1.9 g para-toluensulphonic acid dissolved in 10 ml methyl-ethyl-ketone were added. The solid thus formed was filtered and crystallized from a mixture acetone-water.

Yield: 3 g.

Melting Point: 173°–175° C.

$[\alpha]_D^{20}$: +275° (C=1 in water).

What we claim is:

1. A method of producing derivatives of 6-β-amidinopenicillanic acid having the formula

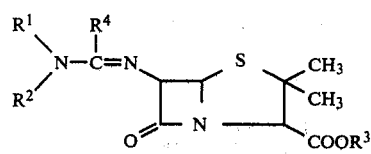 (I)

wherein $R^1$ and $R^2$ are a $C_1$–$C_4$ alkyl group, a $C_5$–$C_6$ cycloalkyl group, or $R^1$ and $R^2$ together with nitrogen atom, to which they are bonded, form a seven member heterocyclic ring or a morpholino ring; $R^3$ is selected from the group consisting of hydrogen and substituted or unsubstituted alkyl; and $R^4$ is selected from the group consisting of hydrogen and $C_1$–$C_4$ alkyl radicals, said method comprising reacting a derivative of 6-aminopenicillanic acid having the formula

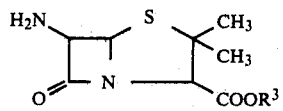 (II)

wherein $R^3$ is as above defined, with a derivative of a disubstituted amide, the reaction being carried out in an inert anhydrous organic solvent selected from the group consisting of methylene chloride and chloroform and in the presence of at least 2 equivalents of a tertiary amine, at a temperature lower than +10° C., wherein said derivative of a disubstituted amide is a complex of a carboxylic acid amide having the formula

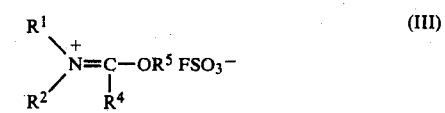 (III)

wherein $R^1$, $R^2$ and $R^4$ are as above defined, and $R^5$ is methyl or ethyl.

2. A method according to claim 1, wherein the radicals $R^1$ and $R^2$ together with nitrogen atom, to which they are bonded, form a heterocyclic ring having 7 atoms, of which 6 are C atoms, and $R^3$ and $R^4$ are both hydrogen atoms.

3. A method according to claim 1, wherein the radicals $R^1$ and $R^2$ together with nitrogen atom, to which they are bonded, form a heterocyclic ring having 7 atoms, of which 6 are C atoms, $R^3$ is —CH$_2$OOCC(CH$_3$)$_3$ and $R^4$ is hydrogen.

4. A method according to claim 3, wherein the compound thus obtained is converted to its hydrochloride.

* * * * *